(12) United States Patent
Kirwan, Jr.

(10) Patent No.: US 11,039,875 B2
(45) Date of Patent: Jun. 22, 2021

(54) NON-STICK MONOPOLAR SUCTION COAGULATOR

(71) Applicant: Kirwan Surgical Products LLC, Marshfield, MA (US)

(72) Inventor: Lawrence T. Kirwan, Jr., Kingston, MA (US)

(73) Assignee: Kirwan Surgical Products LLC, Marshfield, MA (US)

( * ) Notice: Subject to any disclaimer, the term of this patent is extended or adjusted under 35 U.S.C. 154(b) by 519 days.

(21) Appl. No.: 15/138,753

(22) Filed: Apr. 26, 2016

(65) Prior Publication Data

US 2017/0303989 A1 Oct. 26, 2017

(51) Int. Cl.
*A61B 18/14* (2006.01)
*A61B 18/12* (2006.01)
*A61B 18/00* (2006.01)

(52) U.S. Cl.
CPC .......... *A61B 18/14* (2013.01); *A61B 18/1206* (2013.01); *A61B 2018/00589* (2013.01); *A61B 2018/1465* (2013.01); *A61B 2018/1497* (2013.01); *A61B 2218/007* (2013.01)

(58) Field of Classification Search
CPC ................ A61B 18/14; A61B 18/1206; A61B 2018/00589; A61B 2218/007; A61B 2018/1465; A61B 2018/1497
See application file for complete search history.

(56) References Cited

U.S. PATENT DOCUMENTS

| | | | |
|---|---|---|---|
| 3,685,518 A | 8/1972 | Beuerle et al. | |
| 3,902,494 A | 9/1975 | Haberlen et al. | |
| 4,492,231 A | 1/1985 | Auth | |
| 5,089,002 A | 2/1992 | Kirwan, Jr. | |
| 5,133,714 A | 7/1992 | Beane | |
| 5,196,009 A | 3/1993 | Kirwan, Jr. | |
| 5,730,742 A * | 3/1998 | Wojciechowicz | A61B 18/14 604/35 |
| 5,861,002 A * | 1/1999 | Desai | A61B 8/0841 606/139 |
| 5,968,042 A | 10/1999 | Emster | |
| 5,989,249 A | 11/1999 | Kirwan, Jr. | |
| 6,033,397 A * | 3/2000 | Laufer | A61B 18/08 604/105 |
| 6,059,783 A | 5/2000 | Kirwan, Jr. | |
| 6,174,309 B1 * | 1/2001 | Wrublewski | A61B 18/1442 606/45 |
| 6,174,310 B1 | 1/2001 | Kirwan, Jr. | |

(Continued)

FOREIGN PATENT DOCUMENTS

| | | |
|---|---|---|
| EP | 1025808 B1 | 9/2004 |
| EP | 1007111 B1 | 9/2005 |
| WO | 2008057118 A1 | 5/2008 |

*Primary Examiner* — Michael F Peffley
*Assistant Examiner* — Tigist S Demie
(74) *Attorney, Agent, or Firm* — Verrill Dana, LLP

(57) ABSTRACT

A monopolar suction coagulator device is provided for use with a vacuum source and an electrosurgical generator to perform a coagulation procedure and an evacuation procedure at a surgical site. The device includes an active electrode portion at the distal end of a probe, and the probe is formed of a thermally conductive and electrically conductive, non-stick metal material along all or substantially all of its length, to aid in heat dissipation during a coagulation procedure.

16 Claims, 3 Drawing Sheets

(56) References Cited

U.S. PATENT DOCUMENTS

| | | |
|---|---|---|
| 6,234,178 B1 | 5/2001 | Goble et al. |
| 6,293,945 B1 | 9/2001 | Parins et al. |
| 6,298,550 B1 | 10/2001 | Kirwan, Jr. |
| 6,406,476 B1 | 6/2002 | Kirwan, Jr. et al. |
| 6,544,264 B2 | 4/2003 | Levine et al. |
| 6,749,610 B2 | 6/2004 | Kirwan, Jr. et al. |
| 7,789,882 B2 | 9/2010 | Ariola, Jr. et al. |
| 7,879,034 B2 | 2/2011 | Woloszko et al. |
| 7,892,230 B2 | 2/2011 | Woloszko |
| 8,108,994 B2 | 2/2012 | Ariola, Jr. et al. |
| 8,137,345 B2 | 3/2012 | McNall, III et al. |
| 8,216,233 B2 | 7/2012 | McClurken et al. |
| 8,321,019 B2 | 11/2012 | Esch et al. |
| 8,656,585 B2 | 2/2014 | Ariola, Jr. et al. |
| 8,870,864 B2 | 10/2014 | Davison et al. |
| 9,028,490 B2 | 5/2015 | Heard et al. |
| 2002/0049438 A1* | 4/2002 | Sharkey ............. A61B 18/1402 606/41 |
| 2004/0082951 A1* | 4/2004 | O'Halloran ........ A61B 18/1485 606/45 |
| 2005/0187537 A1 | 8/2005 | Loeb et al. |
| 2006/0079873 A1* | 4/2006 | Scopton ............. A61B 17/3478 606/37 |
| 2006/0235377 A1* | 10/2006 | Earley ................ A61B 18/148 606/41 |
| 2010/0010485 A1* | 1/2010 | West, Jr. ............ A61B 18/1482 606/37 |
| 2010/0241114 A1* | 9/2010 | Privitera ................ A61B 18/02 606/21 |
| 2014/0155890 A1 | 6/2014 | Bernard et al. |
| 2014/0276713 A1 | 9/2014 | Hoey et al. |
| 2014/0350555 A1* | 11/2014 | Heard ................ A61B 18/1485 606/49 |

\* cited by examiner

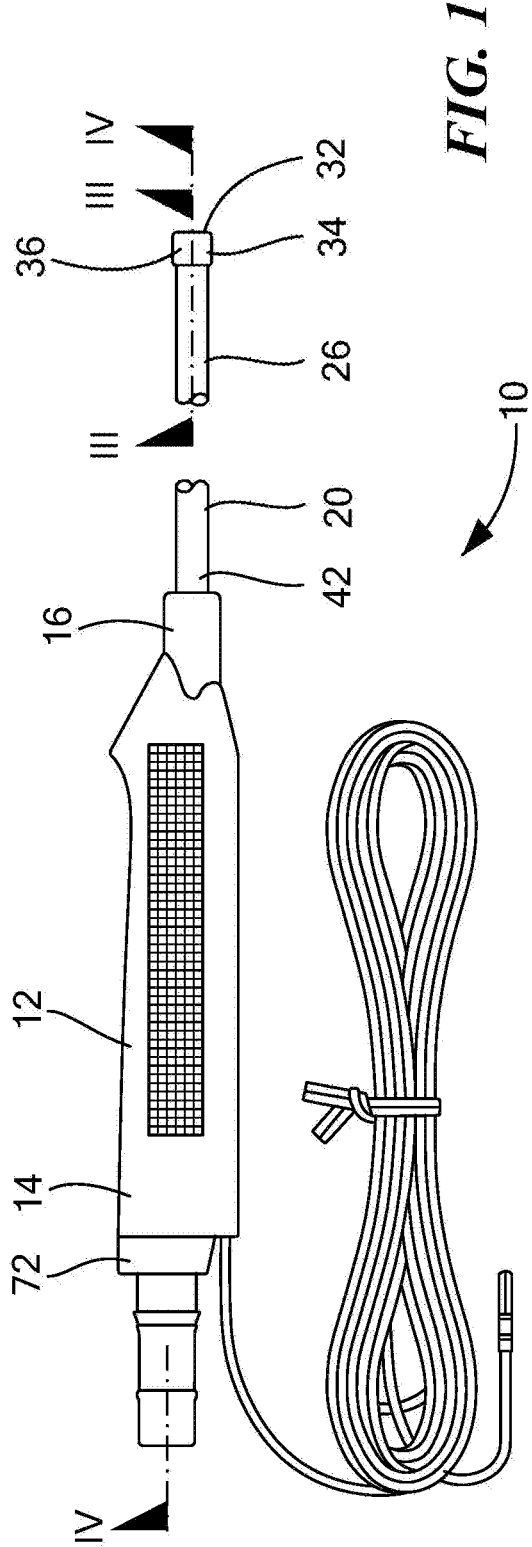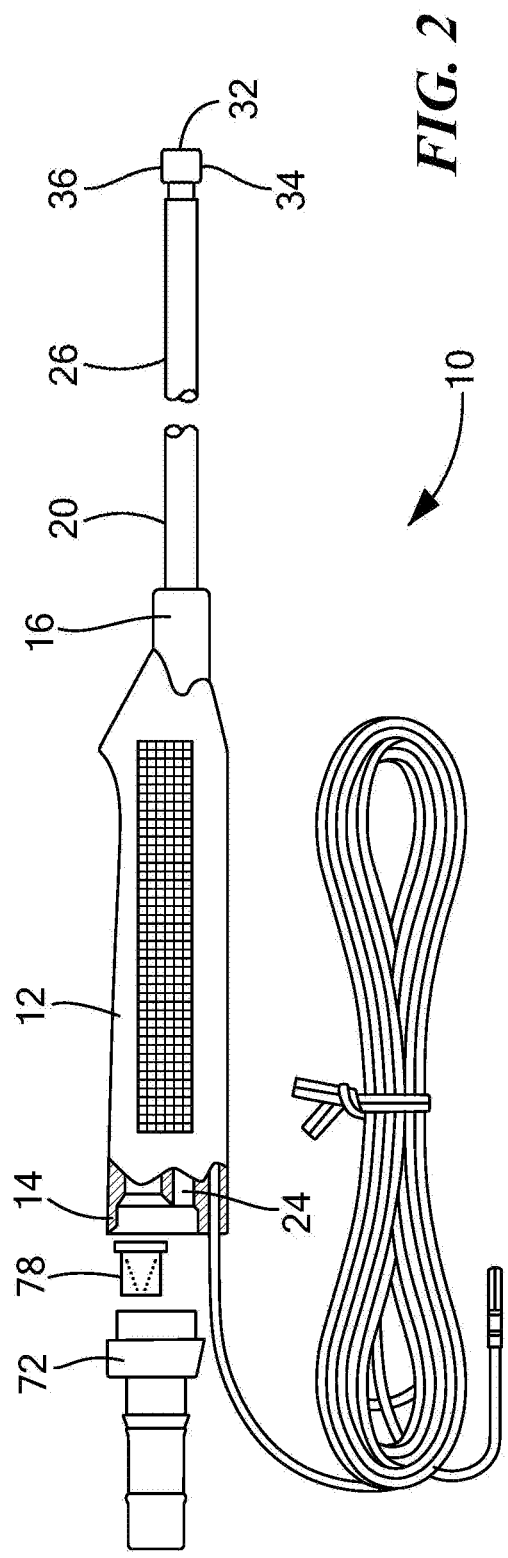

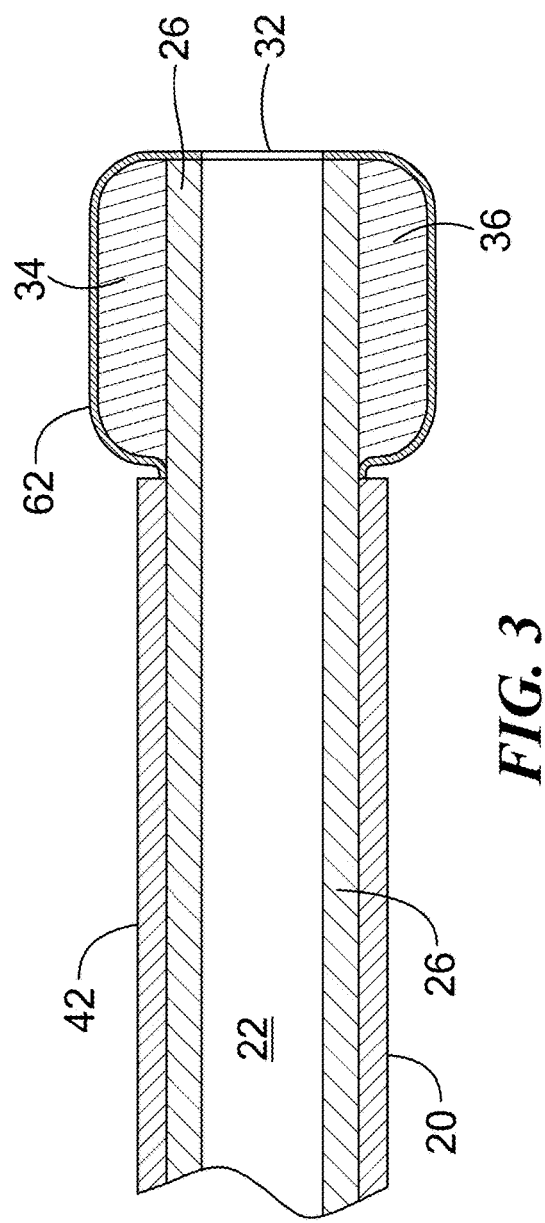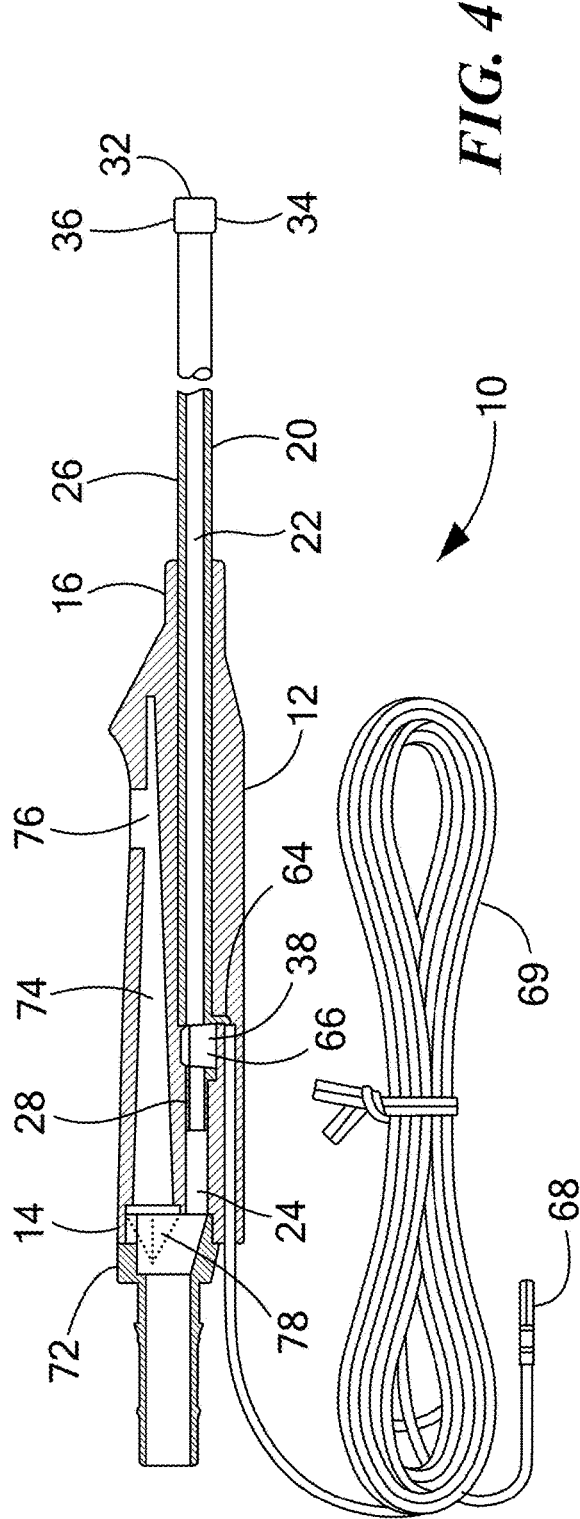

NON-STICK MONOPOLAR SUCTION COAGULATOR

CROSS REFERENCE TO RELATED APPLICATIONS

N/A

STATEMENT REGARDING FEDERALLY SPONSORED RESEARCH OR DEVELOPMENT

N/A

BACKGROUND

In surgical procedures, coagulators are used to coagulate tissue of a patient to stop bleeding. A suction coagulator includes a suction tube connected to a vacuum source to remove tissue and fluids from the region. In a monopolar suction coagulator, a single active electrode, in communication with an electrical generator, is located at the tip of a suction tube or cannula. Current flows from the active electrode through the patient's tissue to a dispersive electrode in contact with the patient's skin (which may be at some distance from the active electrode) and back to the electrical generator. In a bipolar suction coagulator, a suction tube is formed by two coaxial electrodes separated by an insulating material. See U.S. Pat. Nos. 5,089,002; 5,133,714; 5,989,249; 6,174,310; 6,406,476.

Electrosurgical forceps having a pair of tines for grasping tissue are also known to be manufactured with a material to minimize sticking of tissue. See U.S. Pat. Nos. 3,685,518; 4,492,231; 5,196,009; 6,059,783; 6,298,550; 6,749,610; 7,789,882; 8,108,994; 8,656,585.

SUMMARY OF THE INVENTION

The invention relates to a monopolar suction coagulator device for use with a vacuum source and an electrosurgical generator to perform a coagulation procedure and an evacuation procedure at a surgical site of a patient. The device includes an active electrode portion at the distal end of a probe, and the probe is formed of a thermally conductive and electrically conductive, non-stick metal material along all or substantially all of its length, to aid in heat dissipation during a coagulation procedure. By improving heat dissipation, the device can operate effectively to coagulate tissue for a longer period of time and/or for a greater number of uses.

In some embodiments, a monopolar suction coagulator device is provided for use with a vacuum source and an electrosurgical generator to perform a coagulation procedure and an evacuation procedure. The device comprises a housing comprising a distal end and a proximal end, a suction port configured for connection to a vacuum line, and a cavity in the housing in communication with the suction port. A probe extends from the distal end of the housing, and an active electrode portion is disposed at a distal end of the probe. An electrical connection is provided from the probe through the housing to the electrosurgical generator. A suction channel is formed within an interior of the probe from an opening at the distal end of the probe to an opening at a proximal end of the probe in communication with the cavity in the housing. The probe is formed of at least a first material comprising a thermally conductive and electrically conductive non-stick metal, the first material extending along a length of the probe from the distal end toward the proximal end for at least 50% of the length of the probe.

DESCRIPTION OF THE DRAWINGS

The invention will be more fully understood from the following detailed description taken in conjunction with the accompanying drawings in which:

FIG. 1 is a side view of an embodiment of a non-stick-monopolar suction coagulator;

FIG. 2 is an exploded, partially cutaway view of the suction coagulator of FIG. 1;

FIG. 3 is a cross-sectional view along line of FIG. 1;

FIG. 4 is a cross-sectional view along line IV-IV of FIG. 1;

DETAILED DESCRIPTION OF THE INVENTION

Figure 5:
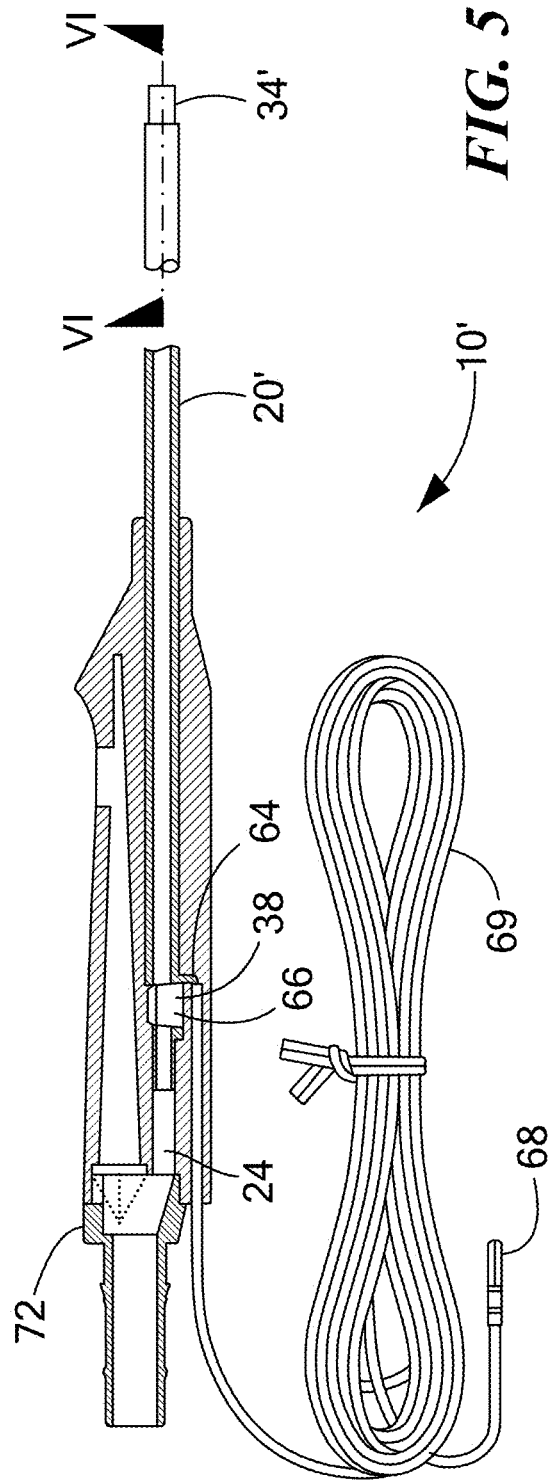
FIG. 5 is a cross-sectional view of a further embodiment of a non-stick monopolar suction coagulator.

One embodiment of a monopolar suction coagulator device 10 is illustrated in FIGS. 1-4. The device includes a housing 12 that extends from a proximal end 14 to a distal end 16 and can be configured for gripping by a hand of a user. The housing is connectable to a vacuum source (not shown) and to an electrosurgical generator (not shown) to perform coagulation procedures and evacuation procedures at a surgical site of a patient. An electrically conductive probe 20 extends from the housing and is connectable through the housing to the electrosurgical generator. The probe also includes a suction channel 22 that is connectable via a cavity 24 in the housing to the vacuum source for evacuation of fluid and residue from the surgical site.

The probe 20 can be formed from a tube 26 having an elongated cylindrical configuration and a hollow interior to form the suction channel 22. The proximal end 28 of the probe is mounted within the housing 12 with the suction channel in communication with the cavity 24 in the housing. (See FIG. 4.) A portion of a length of the probe adjacent to the proximal end is connected to the housing in any suitable manner, such as by insert molding, ultrasonic welding, or adhesive bonding.

The probe 20 is formed from at least a first material comprising a thermally conductive and electrically conductive, non-stick metal material that extends for all or substantially all of the length of the probe, from a distal end 32 toward the proximal end 28. The probe includes an active electrode portion 34 at a distal end for coagulation of a patient's tissue at the surgical site. In the embodiment illustrated in FIGS. 1-4, the active electrode portion includes an enlarged portion or ferrule 36 provided at the tip. An electrical connection 38 is provided from the probe 20 through the housing 12 to the electrosurgical generator. In operation to coagulate tissue during a surgical procedure, electrical current flows through the probe to the active electrode portion while the active electrode portion is brought into contact with tissue to be coagulated. It will be appreciated that, during a surgical procedure, a dispersive electrode (not shown) is provided in contact with the patient's skin (which may be at some distance from the surgical site) for current flow back to the electrical generator. In operation to evacuate a surgical site, a vacuum force is applied to draw fluid and residue into the channel 22 through the distal end 32 and out through the proximal end 28.

At least the working length of the probe, the length extending beyond the housing, can be covered with an electrically insulating material 42. The active electrode portion 34 at the distal end 32 is preferably not covered with an insulating material. The electrically insulating material 42 can be a thermoplastic polymer that can withstand the elevated temperatures to which the device is subject. Suitable electrically insulating materials can include, for example and without limitation, polyethylene, nylon, polyolefin, polyimide, polypropylene, parylene, polytetrafluoroethylene, or polyvinylidene fluoride.

As noted above, the probe 20 is formed of a thermally conductive and electrically conductive metal material that is also non-sticking to tissue. More particularly, the material is provided in a volume that significantly increases the heat capacitance of the probe. The volume of material is provided by extending the material along all or substantially all of the length of the probe. In some embodiments, substantially all of the length of the probe is at least 50%, at least 60%, at least 70%, at least 80%, at least 90%, or at least 95% of the length.

By way of further explanation (while not wishing to be bound by theory), the probe presents an enlarged volume of material to the coagulation site to more rapidly dissipate heat from the coagulation site, thereby preventing excessive heat buildup and minimizing sticking of tissue to the electrode. (Sticking of tissue to the electrode begins when the temperature of the electrode reaches about 60° C.) The heat capacity of a material is the density of the material multiplied by its specific heat. The heat capacitance of a material is its heat capacity multiplied by the volume of the material. The temperature rise per unit of heat (calories) absorbed is the inverse of the heat capacitance. Thus, the larger the volume of a material is, the greater the heat capacitance is. The larger the heat capacitance, the smaller the temperature rise per unit of heat absorbed. Thermal properties of some materials are provided in Table 1.

TABLE 1

Thermal Properties at Room Temperature

| Material | Thermal Conductivity (cal/sec)/(cm$^2$ C./cm) | Specific Heat cal/gram-° C. | Heat Capacity cal/cm$^3$-° C. |
|---|---|---|---|
| Copper | 1.03 | 0.092 | 0.824 |
| Gold | 0.75 | 0.0301 | 0.582 |
| Silver | 1.06 | 0.0561 | 0.589 |
| Stainless Steel 420 | 0.03 | 0.110 | 0.855 |

By using a material with a high thermal conductivity over a greater length of the probe, the heat conducted to the electrode portion from the heated tissue can be distributed over the greater volume of the probe, allowing the entire heat capacitance of the probe to aid in reducing the temperature rise during a coagulation procedure.

Suitable thermally and electrically conductive non-stick metal materials include commercially pure copper, silver, gold, and alloys of copper, silver, and gold. Suitable alloys include, without limitation, silver/copper; silver/gold; silver/palladium, silver/cadmium; silver/cadmium oxide; copper/nickel; copper/beryllium; copper/nickel/beryllium. In some embodiments, an alloy includes at least 50%, at least 60%, at least 70%, at least 80%, at least 90%, at least 95%, at least 97%, at least 98%, or at least 99% of one of copper, silver, and gold.

In some embodiments, the length of the probe 20 from the distal end to the proximal end can range from 8 to 9 inches. In some embodiments, the working length of the probe, the length extending outside of the distal end of the housing, can range from 4 to 6 inches. In some embodiments, the working length is 5.5 inches. In some embodiments, an inner diameter of the thermally and electrically conductive non-stick metal material can range from 0.06 to 0.125 inch, and an outer diameter can range from 8 French to 15 French. The cylindrical tube of the thermally and electrically conductive non-stick metal can be formed in any suitable manner, such as by extrusion.

The enlarged active electrode portion 34 illustrated in FIGS. 1-4 can be formed in any suitable manner. In some embodiments, the probe 20 is a cylindrical tube, and the active electrode portion 34 is a ferrule 36 surrounding the distal end 32 of the cylindrical tube, as shown more particularly in FIG. 3. The ferrule can have a length ranging from 0.125 to 0.25 inch and an outer diameter ranging from 0.125 to 0.25 inch. The ferrule can be attached to the distal end of the tube in any suitable manner to maintain electrical conductivity between the ferrule and the tube, such as by soldering, swaging, or welding. The ferrule can be made of any suitable thermally conductive and electrically conductive non-stick metal material, as described above. In some embodiments, the probe and the ferrule are formed of the same material. In some embodiments, the enlarged electrode portion and the cylindrical tube of the probe can be formed unitarily from a single piece of material.

Figure 6:
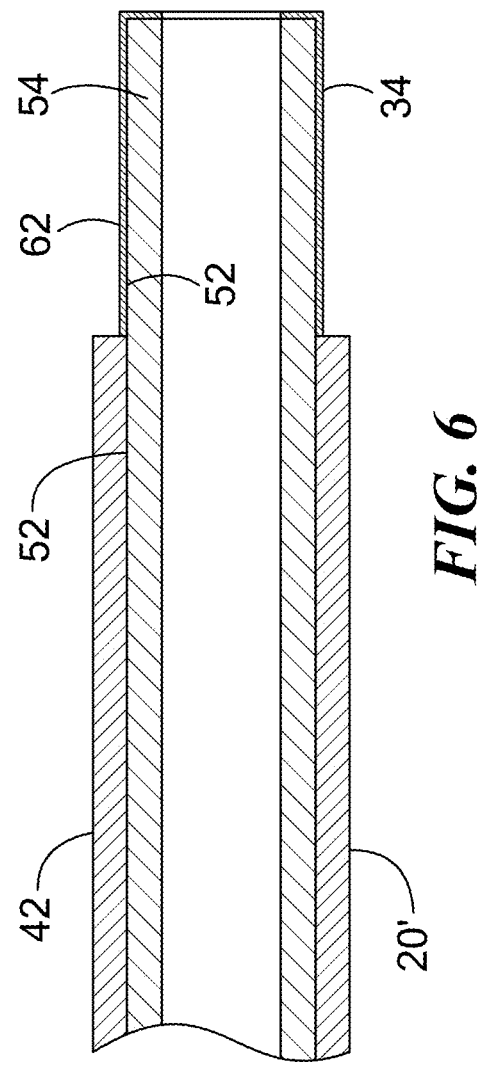
FIG. 6 is a cross-sectional view along line VI-VI of FIG. 5.

Referring to FIGS. 5 and 6, in some embodiments of a device 10', a probe 20' can include a thermally and electrically conductive non-stick metal material coaxially formed as a coating 52 over another layer 54 made of an electrically and thermally conductive material. The coating can be provided along all or substantially all of the length of the probe, as described above. In some embodiments, the coating can be formed as a plating, by any conventional plating process. The plating can have a thickness ranging from 0.0002 to 0.005 inch, and the underlying material can have a thickness ranging from 0.01 to 0.02 inch. In some embodiments, the probe can be a cylindrical tube of aluminum plated with a copper layer. The active electrode portion 34' can be formed by the distal tip of the probe left free of electrical insulation 42. The active electrode portion can have a length ranging from 0.125 to 0.25 inch.

A plating 62 of an electrically and thermally conducting biocompatible material, such as gold, can be provided over the active electrode portion. A gold plating prevents tarnishing of the material(s) beneath it. The gold plating layer may be made from a variety of gold alloys. In some embodiments, the gold plating layer is made from 24 karat hard gold. The plating can be formed by conventional plating processes, and can have a thickness ranging from 0.0001 to 0.001 inch. Other electrically and thermally conductive materials that are biocompatible with human tissue, such as rhodium, can be used.

Referring to FIGS. 4 and 5, in some embodiments, the electrical connection 38 to the probe 20 can include a wire 64 that is electrically connected to a proximal end of the probe at a location within the housing. For example, an end of the wire can be crimped to the proximal end of the probe with a splice 66. The wire can extend to a connection 68 at an opposite end that is connectable to the electrosurgical generator. In some embodiments, a length of the wire 69, suitably insulated, can extend outside of the housing and the connection 68 can include a pin that can be plugged into the electrosurgical generator. Other configurations of electrical connection can also be provided. For example, in some embodiments, a jumper wire can be provided between the probe and a terminal pin that is affixed to and extends from the housing, and an external electrical cord from the electrosurgical generator can be provided with a socket to connect to the terminal pin on the housing.

A suction port 72 can be provided in the housing for connection to a vacuum line that originates at a vacuum source. The probe 20 is connected to the housing such that the suction channel 24 in the probe is in communication with the cavity in the housing, enabling fluid and residue at the surgical site to be drawn into the probe, through the cavity, and out the suction port when a vacuum force is applied. The suction channel can have any suitable inner diameter.

The vacuum force can be applied and controlled in any suitable manner. In some embodiments, the housing can include a channel 74 from an opening 76 in the housing to a valve 78, such as a duckbill valve, that opens with an applied vacuum force, allowing air to be pulled through the opening. The opening is sized to be covered by a user's thumb, such that when the opening is covered, the duckbill valve closes, and the suction force through the channel is stopped, while the suction force through the probe is increased. In this manner, fluid and residue from the surgical site can flow through the probe. When the user uncovers the opening, the suction force increases through the channel and decreases through the probe sufficiently such that fluid and residue at the surgical site are no longer drawn through the probe.

In some embodiments, the probe can also be formed to be malleable, such that the probe can be bent by the user to better reach a surgical site.

It will be appreciated that the device can be used at surgical sites of both humans and non-human animals.

Further Aspects and Embodiments

Further aspects and embodiments of the invention include the following:
1. A monopolar suction coagulator device for use with a vacuum source and an electrosurgical generator to perform a coagulation procedure and an evacuation procedure, the device comprising:
  a housing comprising a distal end and a proximal end, a suction port configured for connection to a vacuum line, and a cavity in the housing in communication with the suction port;
  a probe extending from the distal end of the housing;
  an active electrode portion disposed at a distal end of the probe, an electrical connection from the probe through the housing to the electrosurgical generator; and
  a suction channel formed within an interior of the probe from an opening at the distal end of the probe to an opening at a proximal end of the probe in communication with the cavity in the housing;
  wherein the probe is formed of at least a first material comprising a thermally conductive and electrically conductive non-stick metal, the first material extending along a length of the probe from the distal end toward the proximal end for at least 50% of the length of the probe.
2. The device of item 1, wherein the first material extends along a length of the probe from the distal end to the proximal end for at least 60%, at least 70%, at least 80%, at least 90%, or at least 95% of the length of the probe.
3. The device of item 1, wherein the probe is formed of the first material along all of the length of the probe.
4. The device of any of items 1-3, wherein the probe comprises a cylindrical tube formed of the first material.
5. The device of any of items 1-4, wherein the probe comprises a combination of metal materials, the first material comprising a coating coaxially disposed on a further metal material.
6. The device of any of items 1-5, wherein the first material is selected from the group consisting of copper, a copper alloy, silver, a silver alloy, gold, and a gold alloy.
7. The device of any of items 1-6, wherein the probe is malleable.
8. The device of any of items 1-7, wherein the active electrode portion comprises an enlarged portion at the distal end of the probe.
9. The device of any of items 1-8, wherein the probe comprises a cylindrical tube having an outer diameter, and the active electrode portion has an outer diameter larger than the outer diameter of the probe.
10. The device of any of items 1-9, wherein the active electrode portion comprises a ferrule disposed coaxially about the distal end of the probe.
11. The device of item 10, wherein the ferrule is soldered to the distal end of the probe.
12. The device of any of items 1-9, wherein the active electrode portion is unitarily formed with the probe from the first material.
13. The device of any of items 1-12, wherein the electrical connection comprises a wire having a first end electrically connected to the probe within the housing, the wire extending to a connection at a second end connectable to the electrosurgical generator.
14. The device of item 13, wherein the wire extends outside of the housing.
15. The device of any of items 1-14, further comprising an electrically insulating coating surrounding an exterior surface of the probe.
16. The device of item 15, wherein the electrically insulating coating comprises a thermoplastic polymer.
17. The device of any of items 15-16, wherein the electrically insulating coating comprises polyethylene, nylon, polyolefin, polytetrafluoroethylene, or polyvinylidene fluoride.
18. The device of any of items 15-17, wherein the active electrode portion is uncoated with the electrically insulating coating.
19. The device of any of items 1-18, wherein the housing further includes a suction control element to control suction through the probe.
20. The device of any of items 1-19, wherein the housing is configured for gripping by a hand of a user.
21. A method of using the device of any of items 1-20, comprising applying an electric current flow through the probe to coagulate tissue at a surgical site of a patient.
22. The method of item 21, further comprising applying a vacuum force to draw fluid and residue into the suction channel from the surgical site.
23. A method of using the device of any of items 1-20, comprising applying a vacuum force to draw fluid and residue into the suction channel from a surgical site of a patient.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A monopolar suction coagulator device for use with a vacuum source and an electrosurgical generator to perform a coagulation procedure and an evacuation procedure, the device comprising:
   a housing comprising a distal end and a proximal end, a suction port configured for connection to a vacuum line, and a cavity in the housing in communication with the suction port;
   a probe comprising a cylindrical tube extending from the distal end of the housing, the cylindrical tube defining a longitudinal axis;
   an active electrode portion disposed coaxially about the longitudinal axis and surrounding a distal end of the probe and having an outer diameter larger than the outer diameter of the probe, and a coaxial extent ending at the distal end of the probe;
   an electrical connection from the probe through the housing to the electrosurgical generator; and
   a suction channel formed within an interior of the probe from a distal opening at the distal end of the probe to a proximal opening at a proximal end of the probe in communication with the cavity in the housing;
   wherein the probe is formed of at least a first material comprising a thermally conductive and electrically conductive non-stick metal, the first material extending along a length of the probe from the distal end toward the proximal end for at least 50% of the length of the probe, and the active electrode portion is in a direct coaxial electrical and thermal connection with the distal end of the probe.

2. The device of claim 1, wherein the probe is formed of the first material along all of the length of the probe.

3. The device of claim 1, wherein the probe comprises a combination of metal materials, the first material comprising a coating coaxially disposed on a further metal material.

4. The device of claim 1, wherein the first material is selected from the group consisting of copper, a copper alloy, silver, a silver alloy, gold, and a gold alloy.

5. The device of claim 1, wherein the probe is malleable.

6. The device of claim 1, wherein the active electrode portion comprises a ferrule disposed coaxially about the distal end of the probe.

7. The device of claim 6, wherein the ferrule is soldered to the distal end of the probe.

8. The device of claim 1, wherein the active electrode portion is unitarily formed with the probe from the first material.

9. The device of claim 1, wherein the electrical connection comprises a wire having a first end electrically connected to the probe within the housing, the wire extending to a connection at a second end connectable to the electrosurgical generator.

10. The device of claim 9, wherein the wire extends outside of the housing.

11. The device of claim 1, further comprising an electrically insulating coating surrounding an exterior surface of the probe.

12. The device of claim 11, wherein the electrically insulating coating comprises a thermoplastic polymer.

13. The device of claim 11, wherein the electrically insulating coating comprises polyethylene, nylon, polyolefin, polytetrafluoroethylene, or polyvinylidene fluoride.

14. The device of claim 11, wherein the active electrode portion is uncoated with the electrically insulating coating.

15. The device of claim 1, wherein the housing further includes a suction control element to control suction through the probe.

16. The device of claim 1, wherein the housing is configured for gripping by a hand of a user.

* * * * *